(12) United States Patent
Singh et al.

(10) Patent No.: US 6,339,171 B1
(45) Date of Patent: Jan. 15, 2002

(54) REMOVAL OR REDUCTION OF PERMANGANATE REDUCING COMPOUNDS AND ALKYL IODIDES FROM A CARBONYLATION PROCESS STREAM

(75) Inventors: Madan Singh; George A. Blay, both of Corpus Christi; Michael L. Karnilaw; Melchior A. Meilchen, both of Houston, all of TX (US); Robin Suzanne Tanke, Stevens Point, WI (US); G. Paull Torrence, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/303,986

(22) Filed: May 3, 1999

Related U.S. Application Data

(63) Continuation-in-part of application No. 08/951,952, filed on Oct. 17, 1997, which is a continuation-in-part of application No. 08/735,361, filed on Oct. 18, 1996, now abandoned.

(51) Int. Cl.$^7$ .................... C07C 51/12; C07C 53/08; C07C 51/42
(52) U.S. Cl. .................. 562/519; 562/607; 562/608
(58) Field of Search ................. 562/608, 607, 562/519

(56) References Cited

U.S. PATENT DOCUMENTS

| 3,769,329 A | 10/1973 | Paulik et al. ............... 260/488 |
| 5,001,259 A | 3/1991 | Smith et al. ............... 562/519 |
| 5,026,908 A | 6/1991 | Smith et al. ............... 562/519 |
| 5,144,068 A | 9/1992 | Smith et al. ............... 562/519 |

FOREIGN PATENT DOCUMENTS

| CN | 079461 A | 6/1992 |
| EP | 161874 B2 | 11/1985 |
| EP | 487284 B1 | 5/1992 |
| EP | 687662 A2 | 12/1995 |
| JP | 61-2052 | 1/1986 |
| JP | 6-156151 | 3/1986 |
| JP | 4-201464 | 7/1992 |
| JP | 4-338357 | 11/1992 |
| JP | 5-140024 | 6/1993 |
| JP | 5-169204 | 7/1993 |
| JP | 5-169205 | 7/1993 |
| JP | 9-40590 | 10/1997 |

OTHER PUBLICATIONS

CRC Press, 56th Ed., Periodic Table.
Watson, Derrick, J., "The Cativa Process for the Production of Acetic Acid", *Catalysis of Organic Reactions*, 75, pp. 369–380 (1998).

*Primary Examiner*—Rosalynd Keys
(74) *Attorney, Agent, or Firm*—M. Susan Spiering; James J. Mullen

(57) ABSTRACT

Disclosed is a method to manufacture high purity acetic acid. Although described in relation to that produced by a low water carbonylation process the present invention is applicable to other mechanisms for production of acetic acid which results in formation of permanganate reducing compounds such as acetaldehyde and its derivatives, and alkyl iodide impurities in intermediate process streams. It has been found that permanganate reducing compounds and alkyl iodides may be conveniently removed from a light phase of an intermediate stream in the reaction process by employing a multiple distillation process coupled with an optional post extraction of acetaldehyde. The distillation process involves first distilling a light phase to concentrate the permanganate reducing compounds, and in particular the acetaldehyde, and then separating the permanganate reducing compounds and alkyl iodides in a second distillation tower. The second distillation serves to remove the permanganate reducing compounds and alkyl iodides from methyl iodide, methyl acetate, and methanol mixture. As an optional third step, the twice distilled stream may be directed to an extractor to recover any remaining quantities of methyl iodide from the aqueous acetaldehyde waste stream. This process affords a final product in greater than 99% purity.

Figure 1:
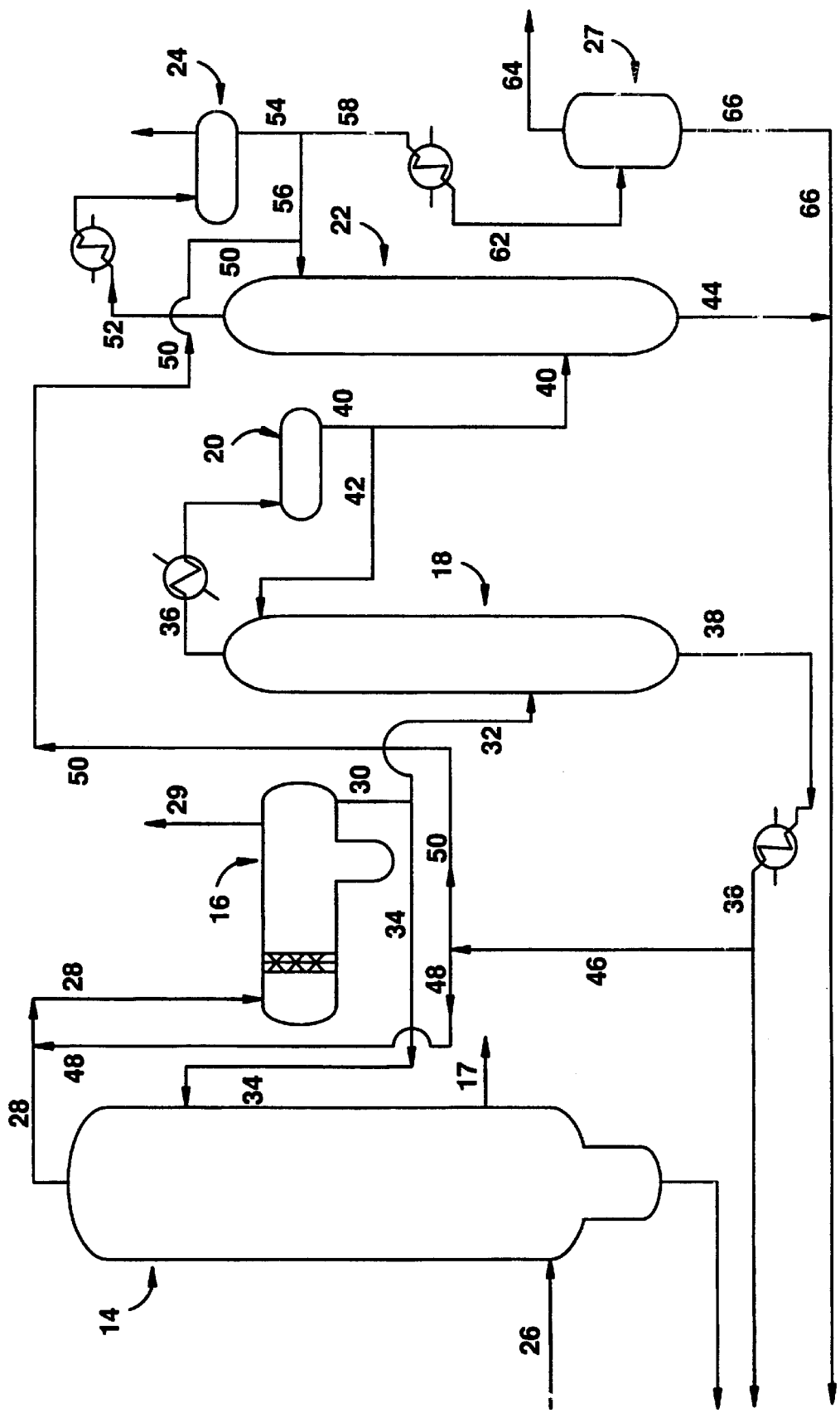

It has been found that during shut down of the inventive process, higher molecular weight polymers of acetaldehyde tend to form in the base of the second distillation tower. To avoid or minimize the formation of these polymers, a constant flow of solvent is passed through the base of the column.

5 Claims, 1 Drawing Sheet

REMOVAL OR REDUCTION OF PERMANGANATE REDUCING COMPOUNDS AND ALKYL IODIDES FROM A CARBONYLATION PROCESS STREAM

CROSS REFERENCE TO RELATED APPLICATIONS

This is a CIP of U.S. Ser. No. 08/951,952 filed Oct. 10, 1997 pending, which was a CIP of 08/735,361 filed Oct. 10, 1996 now abandoned.

FIELD OF INVENTION

This invention relates to a novel process for the removal of permanganate reducing compounds and alkyl iodides formed by the carbonylation of methanol in the presence of a Group VIII metal carbonylation catalyst. More specifically, this invention relates to a novel process for reducing and/or removing precursors of permanganate reducing compounds and alkyl iodides from intermediate streams during the formation of acetic acid by said carbonylation processes.

BACKGROUND OF THE INVENTION

Among currently employed processes for synthesizing acetic acid one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium or else supported on an inert solid, along with a halogen containing catalyst promoter as exemplified by methyl iodide. The rhodium can be introduced into the reaction system in any of many forms, and it is not relevant, if indeed it is possible, to identify the exact nature of the rhodium moiety within the active catalyst complex. Likewise, the nature of the halide promoter is not critical. The patentees disclose a very large number of suitable promoters, most of which are organic iodides. Most typically and usefully, the reaction is conducted with the catalyst being dissolved in a liquid reaction medium through which carbon monoxide gas is continuously bubbled.

An improvement in the prior art process for the carbonylation of an alcohol to produce the carboxylic acid having one carbon atom more than the alcohol in the presence of a rhodium catalyst is disclosed in commonly assigned U.S. Pat. Nos. 5,001,259, issued Mar. 19, 1991; 5,026,908, issued Jun. 25, 1991 and 5,144,068, issued Sep. 1, 1992 and European patent 161,874 B2, published Jul. 1, 1992. As disclosed therein acetic acid is produced from methanol in a reaction medium comprising methyl acetate, methyl halide, especially methyl iodide, and rhodium present in a catalytically effective concentration. The invention therein resides primarily in the discovery that catalyst stability and the productivity of the carbonylation reactor can be maintained at surprisingly high levels, even at very low water concentrations, i.e. 4 weight (wt) % or less, in the reaction medium (despite the general industrial practice of maintaining approximately 14 wt % or 15 wt % water) by maintaining in the reaction medium, along with a catalytically effective amount of rhodium, at least a finite concentration of water, methyl acetate and methyl iodide, a specified concentration of iodide ions over and above the iodide content which is present as methyl iodide or other organic iodide. The iodide ion is present as a simple salt, with lithium iodide being preferred. The patents teach that the concentration of methyl acetate and iodide salts are significant parameters in affecting the rate of carbonylation of methanol to produce acetic acid especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e. resistance to catalyst precipitation, especially during the product recovery steps of the process wherein distillation for the purpose of recovering the acetic acid product tends to remove from the catalyst the carbon monoxide which in the environment maintained in the reaction vessel, is a ligand with stabilizing effect on the rhodium. U.S. Pat. Nos. 5,001,259, 5,026,908 and 5,144,068 are herein incorporated by reference.

It has been found that a low water carbonylation process for the production of acetic acid reduces such by-products as carbon dioxide, hydrogen, and propionic acid. However, the amount of other impurities, present generally in trace amounts, is also increased, and the quality of acetic acid sometimes suffers when attempts are made to increase the production rate by improving catalysts, or modifying reaction conditions.

These trace impurities affect quality of acetic acid, especially when they are recirculated through the reaction process. Among the impurities, which decrease the permanganate time of the acetic acid, are carbonyl compounds, and unsaturated carbonyl compounds. As used herein, the phrase "carbonyl" is intended to mean compounds which contain aldehyde or ketone functional groups which compounds may or may not possess unsaturation. See *Catalysis of Organic Reaction*, 75, 369–380 (1998), for further discussion on impurities in a carbonylation reaction system.

The present invention is directed to reduction and/or removal of permanganate reducing compounds (PRC's) such as acetaldehyde, acetone, methyl ethyl ketone, butyraldehyde, crotonaldehyde, 2-ethyl crotonaldehyde, and 2-ethyl butyraldehyde and the like, and the aldol condensation products thereof. It also leads to reduction of propionic acid. Reduction of other impurities include alkyl iodides such as ethyl iodide, propyl iodide, butyl iodide, pentyl iodide, hexyl iodide, and the like.

It is desirable to remove alkyl iodides from the reaction product since traces of these impurities (in the acetic acid product) tend to poison the catalyst used in the production of vinyl acetate, the product most commonly produced from acetic acid. The present invention is thus also directed to removal of alkyl iodides, in particular $C_{2-12}$ alkyl iodide compounds. The carbonyl impurities may further react with iodide catalyst promoters to form multi-carbon alkyl iodides, e.g., ethyl iodide, butyl iodide, hexyl iodide and the like. Since many impurities originate with acetaldehyde, it is therefore a primary objective to remove or reduce the acetaldehyde and alkyl iodide content in the reaction system.

Conventional techniques to remove impurities include treatment of acetic acid with oxidizers, ozone, water, methanol, activated-carbon, amines, and the like, which treatment may or may not be combined with distillation of the acetic acid. The most typical purification treatment involves a series of distillations of the final product. It is known to remove carbonyl impurities from organic streams by treating the organic streams with an amine compound such as hydroxylamine which reacts with the carbonyl compounds to form oximes followed by distillation to separate the purified organic product from the oxime reaction products. However, the additional treatment of the final product adds cost to the process and it has been found that distillation of the treated acetic acid product can result in additional impurities being formed.

While it is possible to obtain acetic acid of relatively high purity, the acetic acid product formed by the above described low water carbonylation process and purification treatment, frequently remains deficient with respect to the permanganate time. This is due to the presence therein of small proportions of residual impurities. Since a sufficient permanganate time is an important commercial test, which the acid product must meet for many uses, the presence therein of such impurities that decrease permanganate time is objectionable. The removal of minute quantities of these impurities from the acetic acid by conventional treatment and distillation techniques is not economically or commercially feasible by distillation since the impurities have boiling points close to that of the acetic acid product.

It is important to determine where in the carbonylation process impurities can be removed. It is also important to determine by what economically viable process impurities can be removed without risk of further contamination to the final product or unnecessary added costs. JP patent application 5-169205 discloses a method for manufacture of high purity acetic acid by adjusting the acetaldehyde concentration of the reaction solution below 1500 ppm. By maintaining the acetaldehyde concentration in the reaction solution below 1500 ppm, it is stated that it is possible to suppress the formation of impurities and manufacture high purity acetic acid by performing only basic distillation operations during purification of the crude acetic acid formed.

EP 487,284, B1, published Apr. 12, 1995, states that carbonyl impurities present in the acetic acid product generally concentrate in the overhead from the light ends column. Accordingly, the light ends column overhead is treated with an amine compound i.e., hydroxylamine which reacts with the carbonyl compounds to allow such carbonyls to be separated from the remaining overhead by distillation, resulting in an acetic acid product which has improved permanganate time.

EP 0 687 662 A2 describes a process for producing high purity acetic acid whereby an acetaldehyde concentration of 400 ppm or less is maintained in the reactor by removal thereof using a single or multi-stage distillation process. Streams suggested for processing to remove acetaldehyde include a light phase comprising primarily water, acetic acid and methyl acetate; a heavy phase comprising primarily methyl iodide, methyl acetate and acetic acid; an overhead stream comprising primarily methyl iodide and methyl acetate; or a recirculating stream comprising the light and heavy phase combined. Although four streams are suggested for processing, the reference teaches and exemplifies use of the heavy phase. No teaching or suggestion is given regarding which stream(s) possesses the greatest concentration of acetaldehyde.

Also disclosed in EP'662 is management of reaction conditions to control the formation of acetaldehyde in the reactor. By controlling the formation of acetaldehyde, it is stated that reduction of by-products such as crotonaldehyde, 2-ethylcrotonaldehyde, and alkyl iodides are reduced. However, it is pointed out that management of reaction conditions "have a defect to increase a by-production speed of propionic acid." indicating that propionic acid is a problem with the disclosed process of '662.

Hence, EP'662 describes optimization of reaction conditions to avoid formation of acetaldehyde as well as removal of any acetaldehyde beyond a level of 400 ppm formed in the reactor.

While the above-described processes have been successful in removing carbonyl impurities from the carbonylation system and for the most part controlling acetaldehyde levels and permanganate time problems in the final acetic acid product, further improvements can still be made. There remains a need to determine where in the carbonylation process the permanganate reducing compounds, and in particular, acetaldehyde and alkyl iodides are most concentrated and therefore can be reduced or removed so as to insure consistent purity of product. At the same time, there remains a need to provide a process for reduction/removal of such carbonyl materials and iodide compounds without sacrificing the productivity of the carbonylation process or without incurring substantial additional operating costs.

SUMMARY OF THE INVENTION

It has now been discovered that a light ends phase from the light ends distillation column contains carbonyl-containing permanganate reducing compounds, and in particular acetaldehyde which may be further concentrated and removed from the process. In one aspect of this invention, the light ends phase is distilled twice, once through a distillation column which serves to separate the acetaldehyde, methyl iodide, and methyl acetate from acetic acid and water. The second distillation column serves to separate acetaldehyde from methyl iodide and methyl acetate and essentially serves to concentrate and purge the acetaldehyde from the process. Optionally, in another aspect of the invention, the resulting distillate from the second distillation is directed to an extractor to separate out concentrated acetaldehyde and return a residual saturated organic iodide solution to the carbonylation reaction system.

In another aspect of the invention, alkyl iodide compounds, in particular $C_{2-12}$, may be removed or significantly reduced employing the described dual distillation process.

It has been found that when shutting down the carbonylation system, in particular the distillation columns employed in the present process, polymers of acetaldehyde, in particular higher molecular weight polymers tend to form and build up in the base of the second column. Another aspect of the present invention describes a method to deal with this problem. It has been found that a constant flow of solvent to maintain contact between the stream within the second distillation column and a solvent from an internal stream (such as one that contains a large percentage of acetic acid or methyl acetate) results in a polymer-free column base upon shut down of the unit. By having the base devoid of polymer build up, one may shut down and subsequently start up the column in a relatively trouble free, efficient, and cost-effective manner.

The present invention utilizes a light phase, which is an internal, intermediate stream in the process, instead of a heavy phase (as suggested in EP'662), for reduction, or removal of PRC's, their precursors and alkyl iodide compounds. The art traditionally employs a heavy phase for treatment or removal of carbonyl impurities and in particular, removal of acetaldehyde. To date, the art was not aware-that light phase was the better option compared to the heavy phase to reduce PRC's and alkyl iodides. Generally, the art employs an extractor before the second distillation; it has been found that the use of an extractor after the second distillation (or a post-extractor process) results in greater removal of acetaldehyde. It has also been found that due to the dual distillation process, coupled with the post extractor, a very concentrated acetaldehyde stream with essentially no methyl iodide is purged from the process. It has been found that the formation of meta- and paraldehyde in the second column, as well as higher molecular weight polymers thereof, can be inhibited or suppressed by the use of an internal stream comprising approximately 70 wt % water and 30 wt % acetic acid. Because the stream is internal, to the process, it does not place an added water load to the process. It has further been found that the recycle of the first column's residue to the light ends column decanter can be used to extract more PRC's from the heavy phase into the light phase and thus improve acetic acid product quality overall.

A preferred embodiment of the present invention is directed towards a process for reduction and/or removal of permanganate reducing compounds, their precursors, and $C_{2-12}$ alkyl iodide compounds formed in the carbonylation of methanol to a product of acetic acid, wherein said methanol is carbonylated in a suitable liquid phase reaction medium comprising a Group VIII metal catalyst, an organic iodide and iodide salt catalyst promoter; the products of said carbonylation are separated into a volatile phase comprising product, and a less volatile phase comprising Group VIII metal catalyst, acetic acid, and iodide catalyst promoter; said product phase distilled in a distillation tower to yield a purified product and an overhead comprising organic iodide, methyl acetate, water, acetic acid, and unreacted methanol, directing at least a portion of the overhead to an overhead receiver decanter which separates the overhead into a light phase, comprising acetic acid and water, and a heavy phase comprising methyl acetate and organic iodide; and recycling the heavy phase to the carbonylation reactor, the improvement which comprises (a) directing the light phase comprising acetic acid and water to a distiller which separates the mixture into two streams: residue stream (1) comprising primarily water and acetic acid, and overhead stream 2) comprising methyl iodide, methyl acetate, methanol, $C_{2-12}$ alkyl iodides, and permanganate reducing compounds (PRC's);

(b) circulating stream (1) of step (a) to further processing and ultimately back to the reaction system, and stream (2) of step (a) to a second distiller which serves to strip the PRC's and alkyl iodides from the mixture;

(c) optionally, forwarding the over head stream containing PRC's or precursors thereof of step (b) to an extractor and, (d) separating out concentrated PRC's and alkyl iodides for disposal and returning the organic iodide phase of (b) or (c) as a stream containing a lower percentage of PRC's, precursors, and/or $C_{2-12}$ alkyl iodides to the carbonylation reaction system.

The bulk of the overhead from the light phase is recycled to the reactor. Thus, in accordance with the present invention, the inventory of PRC's including acetaldehyde, and alkyl iodides is greatly reduced by this multiple distillation plus optional post extraction process and, at the same time, accomplishing such product quality without substantially increasing the cost of production.

It has been found that PRC's, in particular acetaldehyde, crotonaldehyde, and 2-ethyl crotonaldehyde, and alkyl iodides, in particular hexyl iodide, are reduced by at least 50%, usually greater than that, employing the inventive process. Additionally, propionic acid has been reduced, usually greater than 20%, most often greater than 30% and 40%, and total iodides have been reduced by a percentage reduction of about 50%, most often greater than 60%. The permanganate time has been observed to increase by a percentage of about 50%, usually greater than 70% with the inventive process.

Once the inventive process was operational and shut down of the system was on going, it was discovered that polymers of acetaldehyde, in particular, polymers having a molecular weight greater than about 1000, tended to build up in the second column and plug the column. The polymers were found to be viscous, and thixotropic and tended to adhere to the walls of the column. Upon heating, these polymers tended to crystallize and harden along the walls of the column, making them very difficult to remove. It was found that this problem could be avoided by contacting the stream flowing through the second distillation column with solvent stream flow in an amount sufficient and at a flow rate sufficient to avoid aldol condensation polymer formation or to avoid formation of polymers of acetaldehyde. The solvent may be selected from acetic acid, methyl acetate, methanol, water, methyl iodide and the like or combinations thereof with acetic acid being preferred in view of the abundance of an internal stream to utilize. Generally, amounts sufficient to avoid aldol condensation reactions from occurring are rates of about 0.25–5 gallon per minute (gpm), preferably about 0.5–2 gpm with most preferable rate being about 1 gpm. It is undesirable to use an excess of solvent since this places a greater load on the system to reprocess the excess solvent. Although various positions of ingress of the solvent are acceptable, it is preferred that the solvent be contacted with the stream in the second distillation column at the base of the column.

DRAWINGS

FIG. 1 illustrates a preferred embodiment for the removal of carbonyl impurities from an intermediate stream of the carbonylation process for the production of acetic acid by a carbonylation reaction.

DETAILED DESCRIPTION OF THE INVENTION

The purification process of the present invention is useful in any process used to carbonylate methanol to acetic acid in the presence of a Group VIII metal catalyst such as rhodium and an iodide promoter. A particularly useful process is the low water rhodium catalyzed carbonylation of methanol to acetic acid as exemplified in aforementioned U.S. Pat. No. 5,001,259. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide coordinates with rhodium. The rhodium component of the catalyst system may be provided by introducing into the reaction zone rhodium in the form of rhodium metal, rhodium salts such as the oxides, acetates, iodides, etc., or other coordination compounds of rhodium, and the like.

The halogen-promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol, which is carbonylated. Thus, in the carbonylation of methanol to acetic acid, the halide promoter will comprise methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process comprises the carboxylic acid product. Thus, in the carbonylation of methanol to acetic acid, the preferred solvent is acetic acid.

Water is contained in the reaction medium but at concentrations well below that which has heretofore been thought practical for achieving sufficient reaction rates. It has previously been taught that in rhodium catalyzed carbonylation reactions of the type set forth in this invention, the addition of water exerts a beneficial effect upon the reaction rate (U.S. Pat. No. 3,769,329). Thus most commercial operations run at water concentrations of at least about 14 wt %. Accordingly, it is quite unexpected that reaction rates substantially equal to and above reaction rates obtained with such high levels of water concentration can be achieved with water concentrations below 14 wt % and as low as about 0.1 wt %.

In accordance with the carbonylation process most useful to manufacture acetic acid according to the present invention, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously (U.S. Pat. No. 5,001,259). The concentration of lithium iodide used in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed, which is in the liquid phase, with gaseous carbon monoxide bubbled through a liquid acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be used provided that the salt is sufficiently soluble in the reaction medium to provide the desired level of the iodide. When the iodide is added as a metal salt, preferably it is an iodide salt of a member of the group consisting of the metals of Group IA and Group IIA of the periodic table as set forth in the "Handbook of Chemistry and Physics" published by CRC Press, Cleveland, Ohio, 1975–76 (56th edition). In particular, alkali metal iodides are useful, with lithium iodide being preferred. In the low water carbonylation process most useful in this invention, the additional iodide over and above the organic iodide promoter is present in the catalyst solution in amounts of from about 2 to about 20 wt %, the methyl acetate is present in amounts of from about 0.5 to about 30 wt %, and the lithium iodide is present in amounts of from about 5 to about 20 wt %. The rhodium catalyst is present in amounts of from about 200 to about 2000 parts per million (ppm).

Typical reaction temperatures for carbonylation will be approximately 150 to about 250° C., with the temperature range of about 180 to about 220° C. being the preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

A typical reaction and acetic acid recovery system which is used for the iodide-promoted rhodium catalyzed carbonylation of methanol to acetic acid is shown in FIG. 1 and comprises a liquid phase carbonylation reactor, flasher, and a methyl iodide acetic acid light ends column 14 which has an acetic acid side stream 17 which proceeds to further purification. The reactor and flasher are not shown in FIG. 1. These are considered standard equipment now well known in the carbonylation process art. The carbonylation reactor is typically a stirred vessel within which the reacting liquid contents are maintained automatically at a constant level. Into this reactor there are continuously introduced fresh methanol, carbon monoxide, sufficient water as needed to maintain at least a finite concentration of water in the reaction medium, recycled catalyst solution from the flasher base, a recycled methyl iodide and methyl acetate phase, and a recycled aqueous acetic acid phase from an overhead receiver decanter of the methyl iodide acetic acid light ends or splitter column 14. Distillation systems are employed that provide means for recovering the crude acetic acid and recycling catalyst solution, methyl iodide, and methyl acetate to the reactor. In a preferred process, carbon monoxide is continuously introduced into the carbonylation reactor just below the agitator, which is used to stir the contents. The gaseous feed is thoroughly dispersed through the reacting liquid by this stirring means. A gaseous purge stream is vented from the reactor to prevent buildup of gaseous by-products and to maintain a set carbon monoxide partial pressure at a given total reactor pressure. The temperature of the reactor is controlled and the carbon monoxide feed is introduced at a rate sufficient to maintain the desired total reactor pressure.

Liquid product is drawn off from the carbonylation reactor at a rate sufficient to maintain a constant level therein and is introduced to the flasher. In the flasher the catalyst solution is withdrawn as a base stream (predominantly acetic acid containing the rhodium and the iodide salt along with lesser quantities of methyl acetate, methyl iodide, and water), while the vapor overhead stream of the flasher comprises largely the product acetic acid along with methyl iodide, methyl acetate, and water. Dissolved gases exiting the reactor as a side stream and entering the flasher consist of a portion of the carbon monoxide along with gaseous by-products such as methane, hydrogen, and carbon dioxide and exit the flasher as an overhead stream and are directed to the light ends or splitter column 14 as stream 26.

It has now been discovered that there is a higher concentration, about 3 times, of the PRC's and in particular acetaldehyde content in the light phase than in the heavy phase stream-exiting column 14. Thus, in accordance with the present invention, stream 28, comprising PRC's is directed to an overhead receiver decanter 16 where the light ends phase, stream 30, is directed to distillation column 18.

The present invention may broadly be considered as distilling PRC's, primarily aldehydes and alkyl iodides, from a vapor phase acetic acid stream. The vapor phase stream is twice distilled and optionally post extracted to remove PRC's. Disclosed is a method of removing aldehydes and alkyl iodides and reducing levels of propionic acid, from a first vapor phase acetic acid stream comprising:

a) condensing said first vapor phase acetic acid stream in a first condenser and biphasically separating it to form a first heavy liquid phase product and a first light liquid phase product wherein said first heavy liquid phase contains the larger proportion of catalytic components than said first light liquid phase product;

b) distilling said light liquid phase product in a first distillation column, which distillation is operative to form a second vapor phase acetic acid product stream which is enriched with aldehydes and alkyl iodides with respect to said first vapor phase acetic acid stream;

c) condensing said second vapor phase stream in a second condenser and biphasically separating it to form a second heavy liquid phase product and a second light liquid phase product wherein said second heavy liquid phase product contains a higher proportion of catalytic components than said second light liquid phase product; and d) distilling said second light liquid phase product in a second distillation column wherein said process is operative to reduce and/or remove at least 50% of the alkyl iodide and aldehyde impurities and at least 20% of the propionic acid impurities in said first vapor phase acetic acid stream in an aldehyde and alkyl iodide waste stream.

Referring to FIG. 1, the first vapor phase acetic acid stream (28) comprises methyl iodide, methyl acetate, acetaldehyde and other carbonyl components. This stream is then condensed and separated (in vessel 16) to form a first vapor phase stream to separate the heavy phase product containing the larger proportion of catalytic components—which is recirculated to the reactor (not shown in FIG. 1), and a light phase (30) comprising acetaldehyde, water, and acetic acid. This light phase is subsequently distilled twice to remove the PRC's and primarily the acetaldehyde component of the stream. The light phase (30) is directed to column 18, which serves to form a second vapor phase (36) enriched in aldehydes and alkyl iodides with respect to stream 28. Steam 36 is condensed (vessel 20) and biphasically separated to form a second heavy liquid phase product and a second light phase liquid product. This second heavy liquid phase contains a higher proportion of catalytic components than the second light liquid phase and is subsequently recirculated to the reactor. The second liquid light phase (40) comprising acetaldehyde, methyl iodide, methanol, and methyl acetate is directed to a second distillation column (22) wherein the acetaldehyde is separated from the other components. Catalytic components include methyl iodide, methyl acetate, methanol, and water. This inventive process has been found to reduce and/or remove at least 50% of the alkyl iodide impurities found in an acetic acid stream. It has also been shown that acetaldehyde and its derivatives is reduced and/or removed by at least 50%, most often greater than 60%.

A preferred embodiment of the present invention is shown in FIG. 1; from the top of the light ends or splitter column, 14, vapors are removed via stream 28, condensed, and directed to 16. The vapors are chilled to a temperature sufficient to condense and separate the condensable methyl iodide, methyl acetate, acetaldehyde and other carbonyl components, and water into two phases. The light phase is directed to distillation column 18. Column 18 serves to concentrate the acetaldehyde in stream 32. A portion of stream 30, as stream 34 is directed back to the light ends column, 14, as reflux. A portion of stream 28 comprises noncondensable gases such as carbon dioxide, hydrogen, and the like and can be vented as shown in stream 29 on FIG. 1. Not illustrated in FIG. 1, leaving overhead receiver decanter 16 is also the heavy phase of stream 28. Ordinarily this heavy phase is recirculated to the reactor. However, in another aspect of the invention, a slip stream, generally a small amount, e.g., 25 vol. %, preferably less than about 20 vol. % of the heavy phase is directed to a carbonyl treatment process of this invention and the remainder recycled to the reactor or reaction system. This slip stream of the heavy phase may be treated individually, or combined with the light phase, stream 30 for further distillation and extraction of carbonyl impurities.

Stream 30 enters column 18 as stream 32 in about the middle of the column. Column 18 serves to concentrate the aldehyde components of stream 32 by separating water and acetic acid from the lighter components. In a preferred process of the present invention, stream 32 is distilled in 18, where 18 contains approximately 40 trays, and temperature ranges therein from about 283° F. (139.4° C.) at the bottom to about 191° F. (88.3° C.) at the top of the column. Exiting the top of 18 is stream 36 comprising PRC's and in particular acetaldehyde, methyl iodide, methyl acetate, and methanol, and alkyl iodides. Exiting the bottom of 18 is stream 38 comprising approximately 70% water and 30% acetic acid. Stream 38 is processed, generally cooled utilizing a heat exchanger, is recycled to the light ends column overhead decanter 16 and ultimately to the reactor or reaction system. Stream 36 has been found to have approximately seven times more aldehyde content after the recycle through decanter 16. It has been found that recycling a portion of stream 38 identified as stream 46 back through 16 increases efficiency of the inventive process and allows for more acetaldehyde to be present in the light phase, stream 32. Stream 36 is then directed to an overhead receiver 20 after it has been chilled to condense any condensable gases present.

Exiting 20 is stream 40 comprising acetaldehyde, methyl iodide, methyl acetate, and methanol. A portion of stream 40, i.e., side stream 42 is returned to 18 as reflux. Stream 40 enters distillation column 22 at about the bottom of the column. Column 22 serves to separate the majority of acetaldehyde from the methyl iodide, methyl acetate, and methanol in the stream 40. In an embodiment, column 22 contains about 100 trays and is operated at a temperature ranging from about 224° F. (106.6° C.) at the bottom to about 175° F. (79.4° C.) at the top. In an alternate embodiment, 22 contain structured packing, in place of trays. Preferred packing is a structured packing with an interfacial area of about 65 ft$^2$/ft$^3$, preferably made from a metallic alloy like 2205 or other like packing material, provided they are compatible with the compositions. It was observed during experimentation that uniform column loading, required for good separation, were better with structured packing than with trays. Alternatively, ceramic packing may be employed. The residue of 22, stream 44, exits at the bottom of the tower and is recycled to the carbonylation process.

Acetaldehyde polymerizes in the presence of methyl iodide to form metaldehyde and paraldehyde. These polymers generally are low molecular weight, less than about 200. Paraldehyde has been found to be relatively soluble in the reaction liquid, and primarily in acetic acid. Metaldehyde, upon its precipitation, is a sand-like, granule polymer that is not soluble in the reaction liquid beyond about 3 wt % concentration. Although these polymers are a nuisance for the reaction system, they generally do not require great efforts to remove from the tower once formed.

It has been discovered that during the reaction, and with the heating of column 22, higher molecular weight polymers of acetaldehyde, molecuar weight greater than about 1000, form. These higher molecular weight polymers are believe to come as results of processing the light phase. No literature has been found of formation of these polymers when processing the heavy phase. There has been no indication that these higher molecular weight polymers form when processing the heavy phase. This is a unique problem to processing of the light phase. The higher molecular weight polymers are viscous and thixotropic or do not obey Newtonian fluid laws. As heat is applied to the system, they tend to harden and adhere to the walls of the tower where their removal is cumbersome. Once polymerized they are only slightly soluble in organic or aqueous solvents and removal from the system requires mechanical means. Thus an inhibitor is needed, preferably in tower 22, to reduce the formation of these impurities, i.e., metaldehyde and paraldehyde and higher molecular weight polymers of acetaldehyde (AcH). Inhibitors generally consist of $C_{1-10}$ alkanol, preferably methanol, water, acetic acid and the like used individually or in combination with each other or with one or more other inhibitors. Stream 46, which is a portion of column 18 residue and a slip stream of stream 38, comprises water and acetic acid and hence can serve as an inhibitor. Stream 46 as shown in FIG. 1 splits to form streams 48 and 50. Stream 50 is added to column 22 to inhibit formation of metaldehyde and paraldehyde impurities and higher molecular weight polymers. Since the residue of 22 is recycled to the reactor, any inhibitors added must be compatible with the reaction chemistry. It has been found that small amounts of water, methanol, acetic acid, or a combination thereof, do not interfere with the reaction chemistry and practically eliminate the formation of polymers of acetaldehyde. Stream 50 is also preferably employed as an inhibitor since this material does not change the reactor water balance. Water as an inhibitor is the least preferred solvent of inhibition since large quantities are generally needed to be an effective inhibitor and as such it tends to extract a large amount of acetaldehyde, reducing the purity of stream 52 exiting column 22.

Exiting the top of 22 is stream 52 comprising PRC's. Stream 52 is directed to a condenser and then to overhead receiver 24. After condensation, any non-condensable materials are vented from receiver 24. Exiting 24 is stream 54. Stream 56, a slip stream of stream 54, is used as reflux for 22. Exiting the bottom of 22 is stream 44 comprising methyl iodide, methanol, methyl acetate, methanol and water. This stream is combined with stream 66 and directed to the reactor.

It is important for the extraction mechanism that the top stream of 22 remain cold, generally at a temperature of about 13° C. This stream may be obtained or maintained at about 13° C. by conventional techniques known to those of skill in the art, or any mechanism generally accepted by the industry.

In a preferred embodiment of the present invention, upon exiting 24, stream 54/58 is sent through a condenser/chiller (now stream 62) and then to the extractor 27 to remove and recycle small amounts of methyl iodide from the aqueous PRC stream. Non-condensable gases are vented from the top of 24. In extractor 27, PRC's and alkyl iodides are extracted with water, preferably water from an internal stream so as to maintain water balance within the reaction system. As a result of this extraction, methyl iodide separates from the aqueous PRC's and alkyl iodide phase. In a preferred embodiment, a mixer-settler with a water-to-feed ratio of about 2 is employed.

Exiting the extractor is stream 66 comprising methyl iodide, which is recycled to the reaction system and ultimately to the reactor. The aqueous stream of 64, leaves the extractor from the top thereof. This PRC-rich, and in particular, acetaldehyderich aqueous phase is directed to waste treatment.

The PRC (52) and alkyl iodide-rich phase (44) of the stream stripped from the light phase may optionally be directed to an extractor (27) to remove organic iodide compounds therefrom. The present inventive process has been found to isolate methyl iodide from acetaldehyde for recycling back to the reaction system. Additionally, alkyl iodides such as hexyl iodide have been reduced in the final acetic acid process significantly via the dual distillation process disclosed herein. Hexyl iodide has been reduced by a percent reduction of about 50%, usually greater than 70%. Furthermore, impurities such as crotonaldehyde, 2-ethyl crotonaldehyde were found to be significantly reduced or removed completely from the process. Crotonaldehyde and ethyl crotonaldehyde have been found reduced and/or removed by at least 50%, most often greater than 75% and sometimes 100%. Propionic acid concentration has been found reduced and/or removed by a percent reduction of at least 20%, usually greater than about 30 or 40% when compared to the initial stream removed from vessel 14 (without processing). Total iodides were found reduced by a percent reduction of at least 50%, usually greater than about 60%.

The permanganate time found for the acetic acid product stream once processed through the disclosed method increased about 8-fold, or from about 50%, to greater than 75% or 85% from that product stream not processed as herein described. Data indicates a 50 and 35 second time to increase to about 6 and 5 minutes respectively.

Although the present invention has been generally described above utilizing the light ends phase of column 14, any stream in the carbonylation process having a high concentration of PRC's and alkyl iodides may be treated in accordance with the present invention.

Illustrative alternate embodiments of the present invention, not shown in FIG. 1 include but are not limited to the following:

a) directing an overhead steam from vessel 16 comprising light phase organic material to column 18 and proceeding as described above;

b) directing a residue stream comprising heavy phase organic material from vessel 16 to column 18 and proceeding as described above;

c) directing a stream, preferably a residue stream, from a light ends receiver vent decanter using stream 29, and proceeding as described above;

d) directing a stream from the light ends vent stripper column and proceeding as described above;

e) any combination of the above streams (a–d) which comprise a high concentration of PRC's, propionic acid and alkyl iodide impurities.

Optimization of the inventive process when employing alternate streams may require modification of equipment to achieve maximum efficiency of PRC's and alkyl iodide removal from the carbonylation process. For example, if the same equipment is employed for alternate streams, as for the preferred stream described (i.e. use of stream 28), a taller distillation column 18 may be required to achieve maximum efficiency of removal. If one employs a stream comprising heavy phase components in the inventive process, removal of acetaldehyde may not be as efficient compared to removal of acetaldehyde strictly from a light phase stream.

As previously mentioned, it has been found that when shutting down the carbonylation system, in particular the distillation columns employed in the present process, polymers of acetaldehyde, both low and high molecular weight chain polymers, tend to form and build up in the base of the second column. This is due to the reaction of acetaldehyde and HI present in the column and has been seen to react when the temperature is about 102° C. A constant flow of solvent to maintain contact between the stream within the second distillation column and a solvent from an internal stream (such as one that contains a large percentage of acetic acid or methyl acetate) results in a polymer-free column base during shut down of the column or the PRC/alkyl iodide removal process.

Preferred solvents include those from internal streams containing primarily acetic acid, methyl acetate, methanol, water, methyl acetate, methyl iodide, or combinations thereof. To maintain internal balance within the system, it is preferred to utilize an internal stream, however solvent from an external source may be employed. Since acetic acid is high boiling, it helps strip the acetaldehyde overhead. However, any non-reactant solvent with a normal boiling point greater than or equal to the boiling point of methyl iodide is acceptable. This solvent could be recovered by sending the residue to a recovery device (e.g., stripper, decanter, or permeable membrane).

Overall benefits observed to the final product utilizing the above described process include:

1. increased pernanganate time test values.
2. lower concentration of PRC's;
3. lower total iodides; and,
4. lower propionic acid.

The following Table 1 illustrates data for various PRC's and permanganate time before and after the inventive process was employed. The data was obtained from a crude reactor product stream, and a crude acetic acid product residue stream once the reactor was operating at steady state conditions.

TABLE 1

Data from Reactor Product and Residue Product Stream under Reactor Operating at Steady State Conditions.

| PRC | Before Process | After Process |
|---|---|---|
| Acetaldehyde | 1480 ppm | 596 ppm |
| Crotonaldehyde (res) | 8 ppm | 0 |
| 2-ethyl crotonaldehyde (res) | 7 ppm | 0 |
| Ethyl iodide | 622 ppm | 245 ppm |
| Hexyl iodide (res) | 140 ppb | 22 ppb |
|  | 250 ppb | 30 ppb |
| Total iodide (res) | 225 ppb | 100 ppb |
| Propionic acid (res) | 250 ppm | 150; 130 ppm |
| Permanganate time (res) | 50 seconds | 6 min |
|  | 35 seconds | 5 min | res = residue

What is claimed is:

1. A method to inhibit polymerization of acetaldehyde in a tower during shut down of said tower employed in the carbonylation of methanol to a product of acetic acid, wherein said methanol is carbonylated in a suitable liquid phase reaction medium comprising a Group VII metal catalyst, an organic iodide and iodide salt catalyst promoter; the products of said carbonylation are separated into a volatile phase comprising product, and a less volatile phase comprising Group VIII metal catalyst, acetic acid, and iodide catalyst promoter; said product phase distilled in a distillation tower to yield a purified product and an overhead comprising organic iodide, methyl acetate, water, acetic acid, and unreacted methanol, directing at least a portion of the overhead to a overhead receiver decanter which separates the overhead into a light phase, comprising acetic acid and water, and a heavy phase comprising methyl acetate and organic iodide; and recycling said heavy phase to the carbonylation reactor, the improvement which comprises (a) directing the light phase to a distiller which separates the mixture into two streams: residue stream (1) comprising primarily water and acetic acid, and overhead stream 2) comprising methyl iodide, methyl acetate, methanol, $C_{2-12}$ alkyl iodides, and acetaldehyde;

(b) circulating stream (1) of step (a) to further processing and ultimately back to the reactor, and stream (2) of step (a) to a second distiller which serves to strip the acetaldehyde from the mixture;

(c) contacting stream (2) of step (b) with a stream having a solvent selected from the group acetic acid, methyl acetate, methanol, water, methyl acetate, methyl iodide, or combinations thereof, in an amount sufficient to avoid formation of higher molecular weight polymers of acetaldehyde;

(d) separating out concentrated acetaldehyde for disposal and returning an organic iodide phase to the carbonylation reaction system.

2. The process of claim 1 wherein the solvent is primarily acetic acid.

3. The process of claim 1 wherein the solvent is contacted with stream (2) of step (b) at a rate of about 0.25–5 gallon per minute (gpm).

4. The process of claim 3 wherein the solvent is contacted at a rate of between about 0.5–2 gpm.

5. The process of claim 4 wherein the solvent is contacted with stream (2) of step (b) at the base of the column.

* * * * *